United States Patent [19]
Forster

[11] Patent Number: 4,668,635
[45] Date of Patent: May 26, 1987

[54] METHOD OF DETECTING REATIVE GASES IN A GAS MIXTURE

[75] Inventor: Martin Forster, Jona, Switzerland

[73] Assignee: Cerberus AG, Männedorf, Switzerland

[21] Appl. No.: 713,274

[22] Filed: Mar. 18, 1985

[30] Foreign Application Priority Data

Apr. 4, 1984 [CH] Switzerland ............... 1698/84

[51] Int. Cl.$^4$ ........................................... G01N 21/35
[52] U.S. Cl. ..................................... 436/134; 422/88;
422/91; 422/94; 436/167; 250/343
[58] Field of Search ............... 250/343; 356/432, 437,
356/440; 422/57, 58, 80, 86–88, 91, 94;
436/134, 164, 167

[56] References Cited

U.S. PATENT DOCUMENTS 3,754,867  8/1973  Guenther .
4,063,094  12/1977 Schuman .

FOREIGN PATENT DOCUMENTS 0105659  4/1984  European Pat. Off. .
1017384  10/1957 Fed. Rep. of Germany .
2155111  5/1973  France .

OTHER PUBLICATIONS

Journal "Technisches Messen", vol. 50, 1983, No. 11, pp. 407 to 409; R. E. Neuhäusser: Gaswarngerät mit Photometrischer Auswertung Chemischer Farbreaktionen.
Patents Abstract of Japan, vol. 7, No. 176, Aug. 4, 1983, p. P-214, (1321), and Japanese Patent No. 58-79141.
Rice et al; The Oxidation State of Dispersed Rh on $Al_2O_3$; J. Chem. Phys., 74(11) 6-1-81, pp. 6487–6497.
Cavanagh et al; Site Distribution Studies of Rh Supported on $Al_2O_3$-An Infrared Study of Chemisorbed CO; J. Chem. Phys., 74(7), 4-1-81, pp. 4150–4155.

Primary Examiner—Michael S. Marcus
Assistant Examiner—Michael S. Gzybowski
Attorney, Agent, or Firm—Werner W. Kleeman

[57] ABSTRACT

Reactive gases like, for example reducing gases, specifically carbon monoxide, are detected in a gas mixture, particularly in air, with extremely high sensitivity and with high precision using a gas detector in which the attenuation of the intensity of an infrared radiation beam by a catalyst layer is utilized. Such catalyst layer contains at least one transition metal selected from at least one of the groups I, VII, and VIII of the Periodic Table of the Chemical Elements. Preferably, chemical elements are used having an atomic weight in the range of about 100 to about 205. The detection of carbon monoxide is particularly sensitive using a catalyst layer which substantially contains a metal capable of forming a carboncarbonyl compound with carbon monoxide. The sensitivity and precisionof detecting carbon monoxide and other reducing gases can be significantly increased by periodically exchanging the gas mixture to be investigated in a measuring chamber and replacing it with a pure reference gas from a reference chamber. The sensitivity and precision of the gas detection can be further increased by periodically alternating the temperature of the catalyst layer during such period of gas exchange. The alternating signal this obtained at an output of the gas detector can be evaluated for determining the concentration of the reactive or reducing gases in the investigated gas mixture.

16 Claims, 13 Drawing Figures

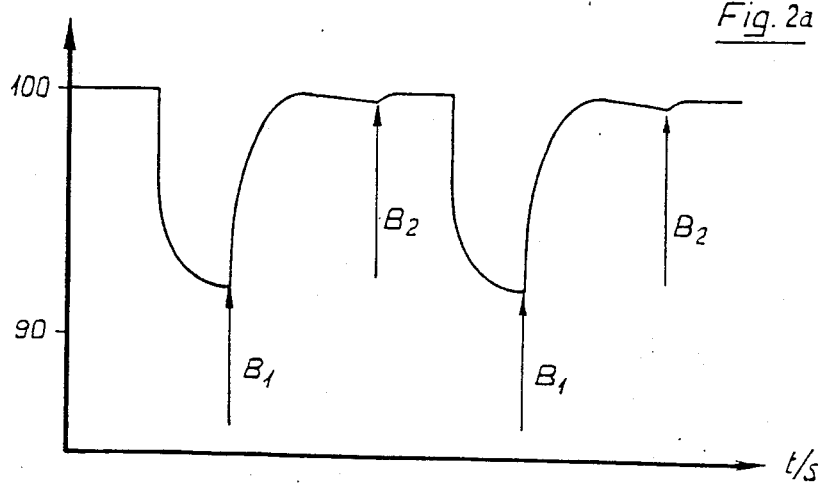
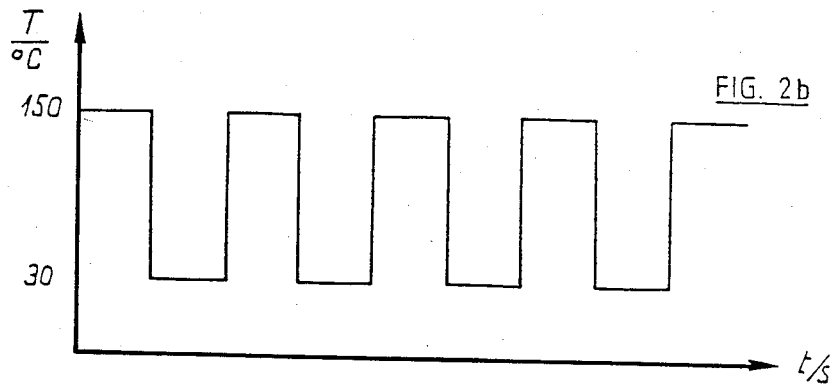
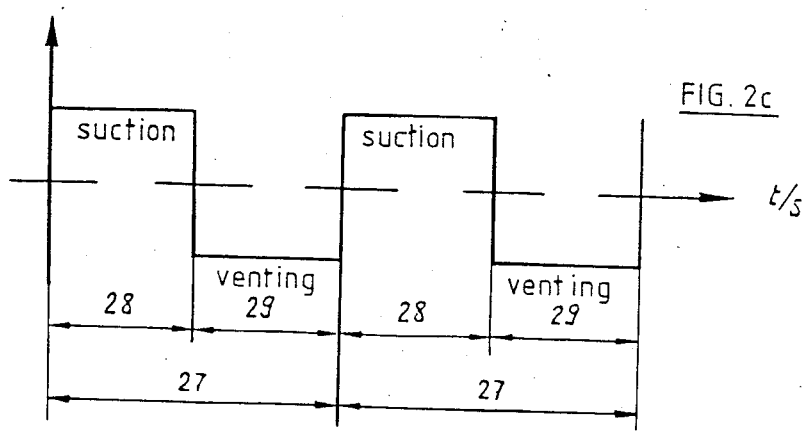

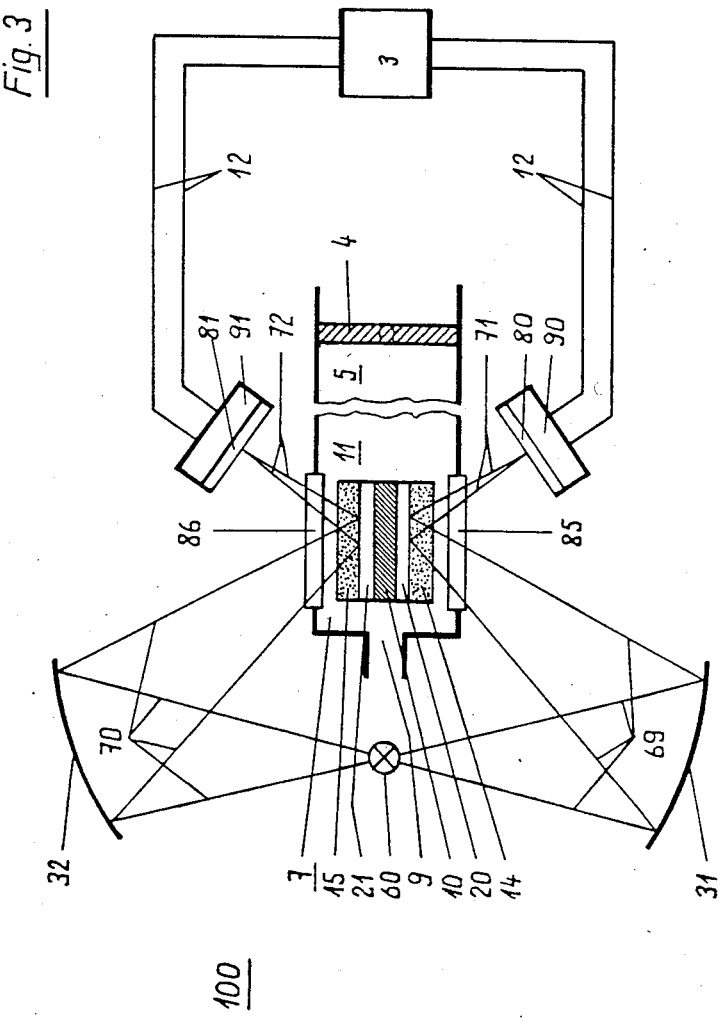

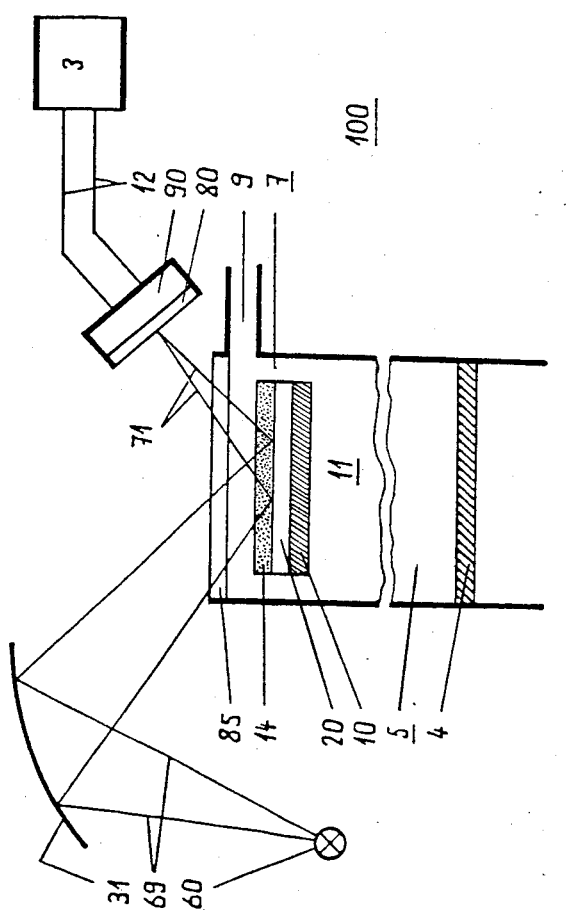

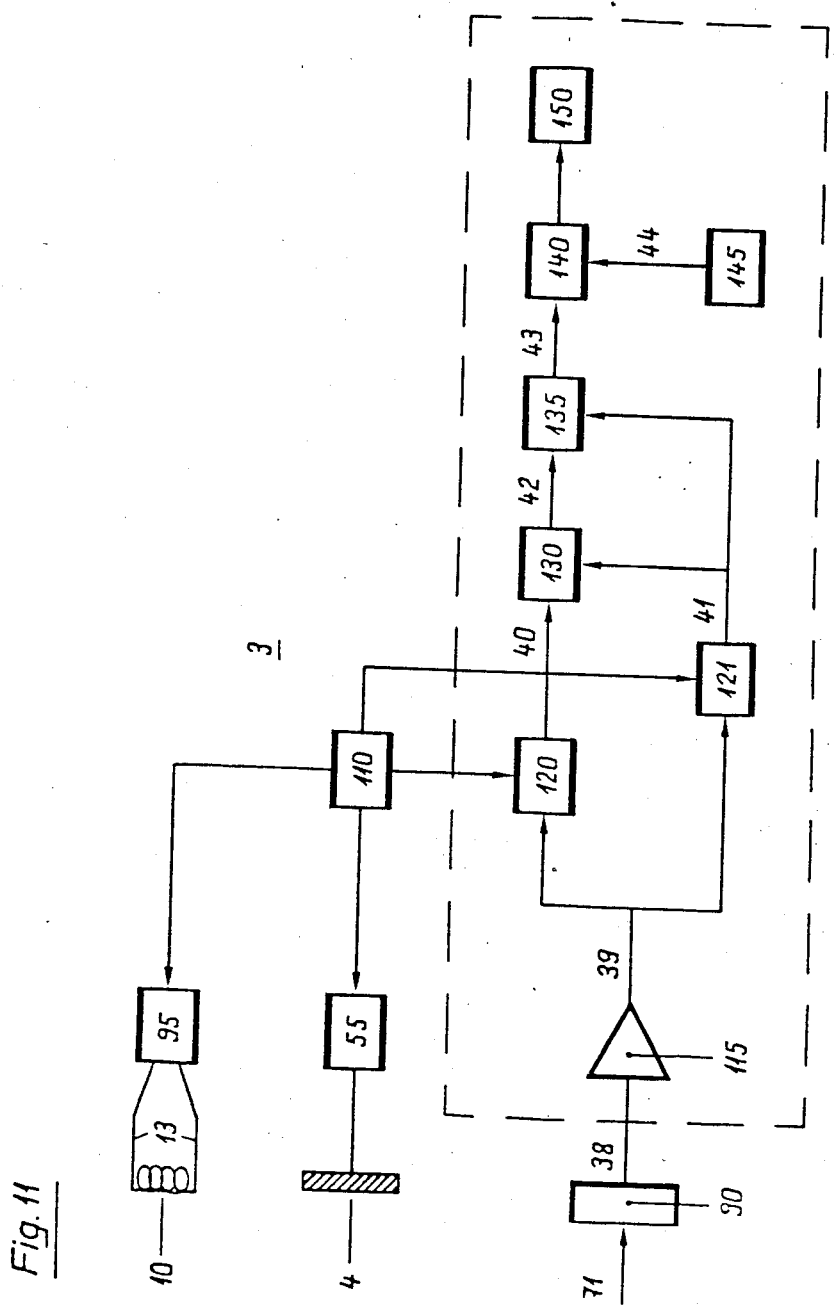

METHOD OF DETECTING REATIVE GASES IN A GAS MIXTURE

CROSS-REFERENCES TO RELATED APPLICATIONS

This application is related to (i) the commonly assigned, copending U.S. application Ser. No. 06/633,652, filed July 23, 1984, entitled METHOD OF PRODUCING CONSTITUENT MATERIALS FOR GAS SENSORS now U.S. Pat. No. 4,579,751, granted Apr. 1, 1986; (ii) the commonly assigned, copending U.S. application Ser. No. 06/635,881, filed July 30, 1984, entitled DEVICE FOR DETECTING GASEOUS CONTAMINANTS IN AIR BY MEANS OF A GAS SENSOR AND METHOD OF PRODUCING SUCH GAS SENSOR; (iii) the commonly assigned, copending U.S. application Ser. No. 06/713,411, filed Mar. 18, 1985, entitled METHOD OF, AND APPARATUS FOR, DETECTING REDUCING GASES IN A GAS MIXTURE and (iv) the commonly assigned, copending U.S. application Ser. No. 06/712,682, filed Mar. 12, 1985, entitled METHOD OF, AND APPARATUS FOR, DETECTING REDUCING GASES IN A GAS MIXTURE The disclosures of these applications are incorporated herein by reference.

BACKGROUND OF THE INVENTION

The present invention relates to a new and improved method of, and apparatus for, detecting at least one reactive gas, particularly at least one reducing gas, and especially although not exclusively carbon monoxide in a gas mixture to be investigated, particularly in air.

In its more particular aspects, the present invention relates specifically to a new and improved method of, and apparatus for, detecting at least one reactive gas, particularly at least one reducing gas, in a gas mixture to be investigated, particularly in air, by means of determining the attenuation of the intensity of an infrared radiation beam in a gas detector which comprises an infrared radiation source, an infrared radiation detector and an electronic evaluation circuit arrangement.

Apparatuses for detecting compounds which preferably absorb electromagnetic radiation, particularly infrared radiation, at certain frequencies are generally known in the field of spectroscopy. Such apparatuses, however, are extremely expensive and, therefore, can not be employed in gas monitoring or alarm installations. For purposes of environmental protection, monitoring garages and parking installations, fire protection, explosion protection and for similar purposes gas detectors are in use for some time. Such gas detectors may comprise inexpensive gas sensors like, for example, pellistors or metal oxide semiconductors which possess an electric conductivity which changes under the action of certain gases. In order to measure the changes in conductivity which occur under the action of the gases to be detected, such gas sensors must have a predetermined minimum size and must be heated to a relatively high temperature. As a result, such gas sensors have a relatively high electric power consumption. The use of the gas sensors in gas monitoring installations is thus restricted since the eventually required emergency power generators would have to be dimensioned in order to generate a correspondingly large amount of power.

There have already been conducted experiments for utilizing the changes in optical properties of metal oxide semiconductors under the action of certain gases for detecting such gases.

It is already known in the scientific literature that, for example, rhodium which is finely distributed on alumina, when exposed to gaseous carbon monoxide, shows a very high infrared extinction coefficient in the region of the carbon monoxide band of gaseous carbon monoxide, see J. Chem. Phys. 74 (07), pages 4150 to 4155, published Apr. 1, 1981. Accordingly, the extinction coefficient in the wave number range of about 1950 to about 2150 $cm^{-1}$ of $Rh(CO)_x$ is about 35 times greater than the extinction coefficient of gaseous carbon monoxide. According to a publication in J. Chem. Phys. 74 (11), pages 6487 to 6497, published June 1, 1981, the compound $Rh(CO)_x$ is also sufficiently stable in the presence of oxygen so that this rhodium compound can also be formed at room temperature. This effect, however, has not been utilized for the detection of reducing gases like, for example, carbon monoxide in gas monitoring installations.

SUMMARY OF THE INVENTION

Therefore, with the foregoing in mind, it is a primary object of the present invention to provide a new and improved method of, and apparatus for, detecting at least one reactive gas, particularly at least one reducing gas and specifically although not exclusively carbon monoxide, in a gas mixture to be investigated, particularly in air, and which uses infrared radiation and in a manner which is not afflicted with the prior art drawbacks and limitations and which is significantly simplified in comparison thereto.

Another and more specific object of the present invention is directed to the provision of a new and improved method of, and apparatus for, detecting at least one reactive gas, particularly at least one reducing gas and specifically although not exclusively carbon monoxide, in a gas mixture to be investigated, particularly in air, and which is more sensitive than the detection based on the investigation of changes in the conductivity of metal oxide semiconductors and which requires considerably less electric power.

Still a further significant object of the present invention is directed to a new and improved method of, and apparatus for, detecting at least one reactive gas, particularly at least one reducing gas and specifically although not exclusively carbon monoxide, in a gas mixture to be investigated, particularly in air, and which is substantially devoid of any zero drift.

Another, still important object of the present invention is directed to a new and improved method of, and apparatus for, detecting at least one reactive gas, particularly at least one reducing gas and specifically although not exclusively carbon monoxide, in a gas mixture to be investigated, particularly in air, and which utilizes a gas detector of significantly smaller geometric dimensions in order to reduce the required heating power.

Now in order to implement these and still further objects of the invention, which will become more readily apparent as the description proceeds, the method of the present development is manifested by the features that, there is used a gas detector comprising a reference chamber which is closed to the external or environmental atmosphere and which is provided with an air or gas displacement means or generator. There is also used a measuring chamber which is connected to the reference chamber by means of at least one connecting aperture or opening and which is provided with an inlet opening for admitting the gas mixture to be investigated. The measuring chamber further contains a gas sensor which can be heated to a predetermined temperature by heating means and which contains at least one transition metal selected from at least one of the groups I, VII and VIII of the Periodic Table of the Chemical Elements. Preferably, the selected transition metal has an atomic weight in the range of about 100 to about 205.

During a suction phase of a periodic operation of the air or gas displacement means the volume of the reference chamber is increased by operating the gas displacement means or generator and the gas mixture to be investigated is periodically drawn through the inlet opening into the measuring chamber and at least partially passed through the measuring chamber into the reference chamber. During a first part of the suction phase the temperature of the gas sensor is so high that any reducing gases which are present, are oxidized. During the remaining part of the suction phase the temperature of the gas sensor is so low that any reducing gases are adsorbed at the gas sensor. As a result, a reference gas which has no or a smaller content of reducing gases is passed through the connecting aperture into the reference chamber.

During a venting phase of the periodic operation of the air or gas displacement means or generator the volume of the reference chamber is decreased by operating the gas displacement generator and the reference gas is periodically vented or blown off and passed through the measuring chamber and through the inlet opening thereof. During a first part of the venting phase the gas sensor has approximately the same temperature at which the reducing gases were oxidized during the suction phase. During the remaining part of the venting phase the gas sensor approximately has the temperature at which the reducing gases were adsorbed during the suction phase.

There is further determined by means of an electric or electronic evaluation circuit arrangement the intensity of an infrared radiation beam which is emitted by the infrared radiation source and which passes through the gas sensor and then forms a measuring beam which impinges upon the infrared radiation detector. A value $B_1$ of the intensity of the measuring beam is measured during the suction phase and preferably at the end of the period of time during which the gas sensor assumes a temperature at which the reducing gases are adsorbed at the gas sensor. A second value $B_2$ of the intensity of the measuring beam is measured during the venting phase and preferably at the end of the period of time during which the gas sensor assumes a temperature at which the reducing gases are adsorbed at the gas sensor. The first value $B_1$ and the second value $B_2$ of the intensity of the measuring beam can be used for detecting the presence of the at least one reducing gas. Such intensities can also be utilized for determining the concentration of the reducing gases which are present in the gas mixture to be investigated.

The electronic evaluation circuit arrangement can also be designed in such a manner that an alarm is triggered at a predetermined concentration of reducing gases in the gas mixture to be investigated. It is also possible to design the electronic evaluation circuit arrangement in such a manner that an early warning is generated at a predetermined lower concentration of reducing gases in the gas mixture to be investigated and which is used for turning on a suction installation and to warn human beings who are exposed to such gas mixture. The last-mentioned electronic evaluation circuit arrangement is furthermore designed in such a manner that a main alarm is triggered at a predetermined higher concentration of reducing gases like, for example, carbon monoxide in the gas mixture to be investigated and which main alarm then causes evacuation of human beings, the triggering of fire extinguishers and a fire alarm.

The inventive method can be used for the detection of gases in gas monitoring installations as well as for the detection of combustion products in fire detecting installations.

According to a preferred embodiment of the inventive method there is used a gas sensor in the gas detector and the gas sensor comprises at least one of the metals rhodium, rhenium, iridium, platinum, palladium, osmium, ruthenium, silver, or gold. Such metal is supported by a carrier containing at least one oxide selected from at least one of the metals magnesium, calcium, strontium, barium, lanthanum, cerium, thorium, titanium, zirconium, vanadium, niobium, tantalum, chromium, molybdenum, tungsten, manganese, iron, cobalt, nickel, copper, zinc, cadmium, aluminum, indium, silicon, tin, lead, antimony, or bismuth.

Preferably, the metals are present in very finely distributed form, however, they can also be present in the form of a thin metal film.

According to a further preferred embodiment of the inventive method modulated infrared radiation is used in the gas detector and in combination therewith phase-sensitive detection is employed.

In accordance with a further preferred embodiment of the inventive method there is used, for detecting carbon monoxide, a catalyst layer of rhodium supported on alumina. An infrared filter having a transmission range from about 1900 to 2200 $cm^{-1}$ is then arranged rearwardly of the infrared radiation source and/or forwardly of the infrared radiation detector with respect to the direction of the infrared radiation.

According to a further preferred embodiment of the inventive method and for detecting acetylene, there is used a catalyst containing silica-supported palladium and an infrared filter having a transmission range from 2950 to 3150 $cm^1$.

Further catalysts and infrared filters can be selected as follows:

For detecting ethylene, silica-supported palladium and an infrared filter having a transmission range from about 2800 to 3100 $cm^{-1}$; for detecting carbon monoxide alumina-supported rhodium and an infrared filter having a transmission range from about 1900 to 2200 $cm^{-1}$, silica-supported palladium and an infrared filter having a transmission range from about 1850 to 2100 $cm^{-1}$, or silica-supported platinum and an infrared filter having a transmission range from about 1950 to 2150 $cm^{-1}$; for detecting ethylene silica-supported platinum and an infrared filter having a transmission range from about 2750 to about 3050 $cm^{-1}$; for nitrogen monoxide alumina-supported rhodium and an infrared filter having a transmission range from about 1600 to about 1900 $cm^{-1}$.

Further carrier materials which can be used instead of alumina or silica, are tin dioxide, magnesium oxide, zinc oxide and titanium dioxide.

As alluded to above, the invention is not only concerned with the aforementioned method aspects, but also relates to a novel construction of apparatus for the performance thereof. Generally speaking, the inventive apparatus comprises a gas detector for detecting at least one reactive gas, particularly at least one reducing gas, especially although not exclusively carbon monoxide in a gas mixture to be investigated, particularly in air.

To achieve the aforementioned measures the inventive gas detector, in its more specific aspects, comprises:

- a reference chamber which is closed to the external atmosphere and which is provided with a gas displacement generator;
- a measuring chamber which is connected with said reference chamber by at least one connecting aperture and which is provided with an inlet opening for admitting the gas mixture to be investigated;
- a gas sensor arranged within the measuring chamber;
- heating means for heating the gas sensor to a predetermined temperature; and
- a catalyst layer of the gas sensor which contains at least one transition metal selected from at least one of the groups I, VII and VIII of the Periodic Table of the Chemical Elements.

Preferably, the transition metal has an atomic weight in the range of 100 to 205.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein:

FIG. 2a is a graph illustrating the intensity of the infrared radiation as a function of time as measured by the gas detector shown in FIG. 1;

FIG. 2b is a graph showing the variation of the heating temperature as a function of time in the gas detector illustrated in FIG. 1;

FIG. 2c is a graph illustrating the suction phase and the venting phase as a function of time in the operation of the gas displacement generator in the gas detector illustrated in FIG. 1;

FIG. 3 is a schematic cross-sectional view of a second embodiment of the inventive gas detector which constitutes a specific arrangement for detecting one further gas in addition to carbon monoxide;

FIG. 4 is a schematic cross-sectional view of a third embodiment of the inventive gas detector in which a concave reflector is used;

FIG. 11 is a schematic block circuit diagram showing an exemplary embodiment of an electronic evaluation circuit arrangement which can be used in combination with the gas detectors illustrated in FIGS. 1 to 10.

DETAILED DESCRIPTION OF THE PREFERRED EMBODIMENTS

Figure 1:
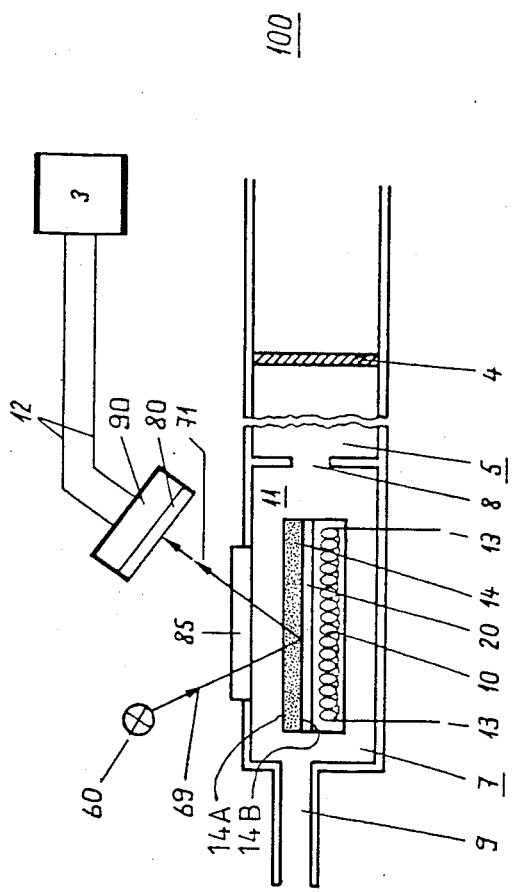
FIG. 1 is a schematic cross-sectional view of a first embodiment of an inventive gas detector for carrying out a first embodiment of the inventive method.

Describing now the drawings, it is to be understood that only enough of the construction of the gas detector has been shown as known for those skilled in the art to readily understand the underlying principles and concepts of the present development, while simplifying the showing of the drawings. Turning attention now specifically to FIG. 1, there has been schematically illustrated in a cross-sectional view a first exemplary embodiment of the inventive gas detector 100 which enables carrying out a first embodiment of the inventive method for detecting a reactive gas, particularly a reducing gas, especially although not exclusively carbon monoxide in a gas mixture like, for example, air. The gas detector 100 essentially comprises a measuring chamber 7 and a reference chamber 5 which is closed to the external or environmental atmosphere. For better recognition of the details the measuring chamber 7 is illustrated at a larger scale. A gas sensor 11 is located within the measuring chamber 7. The gas sensor 11 contains a catalyst layer 14 which can be heated to a predetermined temperature by any suitable heating means 10. Electrical power is supplied to the heating means 10 by an electrical conductor which is connected to a not particularly illustrated power source.

The gas mixture to be investigated is admitted to the measuring chamber 7 through an inlet opening 9. The measuring chamber 7 is connected to the reference chamber 5 by means of a connecting aperture or opening 8. A gas or air displacement generator or gas or air displacement means 4—hereinafter simply referred to as a gas displacement generator or displacement means—is arranged in the reference chamber 5. An infrared window 85 which transmits infrared radiation of a predetermined frequency range is inserted into a sidewall of the measuring chamber 7 which is hermetically sealed from the external or environmental atmosphere with the exception of the inlet opening 9. An infrared radiation beam 69 is emitted by an infrared radiation source 60. The infrared radiation beam 69 enters the measuring chamber 7 through the infrared window 85 and thus impinges upon the gas sensor 11. The infrared radiation beam 69 penetrates the catalyst layer 14 of the gas sensor 11 and is reflected by a reflective layer 20 which is operatively associated with the gas sensor 11 and which is arranged on a side of the gas sensor 11 which is opposite to the side of this gas sensor 11 upon which the infrared radiation beam 69 impinges. Specifically, the infrared radiation beam 69 impinges upon the top side 14A of the catalyst layer 14 and the reflective layer 20 is arranged below or on the bottom side 14B of the catalyst layer 14. The infrared radiation beam 69 is reflected at the reflective layer 20 and thus passes through the catalyst layer 14 of the gas sensor 11 a second time and, as a result, a measuring beam 71 leaves the measuring chamber 7 through the infrared window 85. The measuring beam 71 impinges upon an infrared radiation detector 90.

This infrared radiation detector 90 is connected with an electronic evaluation circuit arrangement 3 by means of conductors or lines 12. The electronic evaluation circuit arrangement 3, which will be described in more detail hereinafter, evaluates the intensity I of the measuring beam 71 measured by means of the infrared radiation detector 90 for determining the concentration of the reactive gas or of the reducing gas which, for example, as previously stated may constitute carbon monoxide. The electronic evaluation circuit arrangement 3 may also be designed in such a manner that an alarm signal is triggered under certain conditions. Furthermore, the electronic evaluation circuit arrangement 3 contains switching elements by means of which there are controlled the movements of the gas displacement means or gas displacement generator 4 and the temperature of the gas sensor 11 via the heating means 10. The switching elements and the connecting lines required therefor are of conventional design and, therefore, not particularly illustrated.

An incandescent light or a commercially available Nernst source is used as the infrared radiation source 60. The infrared window 85 is made of one of the known materials which are transparent for infrared radiation. The infrared window 85 is placed in front of the infrared radiation detector 90 and this infrared window 85 constitutes an infrared filter which transmits infrared radiation in a preselected infrared spectral region from 1900 to 2200 $cm^{-1}$.

The gas displacement means or gas displacement generator 4 is constituted by a commercially available miniaturized loudspeaker.

The gas sensor 11 contains a catalyst layer 14 comprising very finely distributed rhodium which is deposited on alumina. Such catalyst layer 14 is transparent for infrared radiation in the range of 1900 to 2200 $cm^{-1}$. The reflective layer 20 below this catalyst layer 14 is made of gold or any other suitable precious metal at which the infrared radiation beam 69 is reflected.

The catalyst material, namely alumina-supported rhodium is commercially available (Fluka AG, CH-9470 Buchs, Switzerland). For preparing the gas sensor 11, the catalyst material is pressed into a pellet which has a thickness of about 0.5 mm and a diameter of about 13 mm. The pellet is polished on both sides with a suitable abrasive and then with diamond paste to a final thickness of about 0.2 mm. A 3 $\mu$m gold layer is then vapor-deposited on one side of the polished pellet and the thus obtained plate is then cut into pieces of appropriate dimensions. The selected piece is then glued to a heating element which constitutes the heating means 10. A suitable heating element 10 constitutes a thick film resistor made of ruthenium dioxide in a high-temperature stable epoxide resin of any suitable commercially available type.

There will now be described the method of operation of the first exemplary embodiment of the gas detector 100 with reference to FIG. 2.

Using the heating means 10, the gas sensor 11 is heated to a temperature at which the catalyst layer 14 of the gas sensor 11 is capable of catalyzing the oxidation of carbon monoxide to carbon dioxide. This oxidation temperature, for example, may be approximately 150° C. It should be noted, however, that the carbon monoxide must not necessarily be removed by oxidation, but can also be removed by other appropriate chemical reactions or by pumping with the use of a very effective vacuum pump like, for example, an ion or ionization pump. Removal solely by adsorption, however, is insufficient during this phase of the operation. For simplification, there is used hereinafter the term "oxidation-temperature" which relates to the temperature at which the oxidation is catalyzed by the catalyst layer and this term is used to indicate only one of the possible methods of removing carbon monoxide.

Simultaneously with heating the catalyst layer 14 to the aforementioned oxidation temperature, the gas displacement means or generator 4 is operated in such a manner that the volume of the reference chamber 5 is increased. As a result, the gas mixture to be investigated is drawn or sucked into the measuring chamber 7 through the inlet opening 9 and a portion of the gas mixture to be investigated passes through the measuring chamber 7 and through the connecting aperture 8 into the reference chamber 5 during this operation. The intake of the gas mixture to be investigated is continued and during this intake period or suction phase the temperature of the catalyst layer 14 of the gas sensor 11 is lowered to a temperature which is sufficiently low for adsorbing any carbon monoxide present in the gas mixture to be investigated at the gas sensor 11. During the adsorption at the so-called adsorption temperature the carbon monoxide is not oxidized. The adsorption temperature, for example, may be 30° C.

At the termination of the intake period 28, see FIG. 2c, the volume of the reference chamber 5 is decreased by correspondingly operating the gas displacement means or generator 4. The reference gas which is either free of carbon monoxide or which contains a lower concentration of carbon monoxide, is vented through the connecting aperture 8 into the measuring chamber 7, passes through the measuring chamber 7 and through the inlet opening 9 and thus is vented from the gas detector 100. During the start of the venting phase which is designated by reference numeral 29 in FIG. 2c, the temperature of the gas sensor 11 is approximately the same as the temperature at which any present carbon monoxide was oxidized during the suction phase 28, i.e. the temperature of the gas sensor 11 is about 150° C. During the remaining part of the venting phase 29 the temperature of the gas sensor 11 is lowered approximately to the temperature at which any present carbon monoxide was adsorbed during the suction phase 28, i.e. the temperature of the gas sensor 11 is lowered to about 30° C.

The gas exchange period 27 comprising the suction phase 28 and the venting phase 29 is now continuously repeated, and during this repetition of the gas exchange period 27 the temperature of the gas sensor 11 is also periodically varied between the oxidation temperature, for example 150° C. and the adsorption temperature of, for example 30° C.

The intensity I of the measuring beam 71 which is measured by the infrared radiation detector 90 varies also in correspondence to the varying transmission of the catalyst layer 14 of the gas sensor 11 in the region of 1900 to 2200 $cm^{-1}$ during such gas exchange periods 27. The intensity I of the measuring beam 71 is plotted in FIG. 2a in the form of a percentage and as a function of time t.

At the start of the suction phase 28 and during the time during which the gas sensor 11 is maintained at the oxidation temperature, the intensity I of the measuring beam 71 is 100%. When the temperature of the gas sensor 11 is lowered to the adsorption temperature of about 30° C., the transmission of the catalyst layer 14 decreases due to the adsorption of carbon monoxide and as a result the intensity I of the measuring beam 71 assumes a value of $B_1$. After the start of the venting phase 29 the temperature of the gas sensor 11 is again raised to the oxidation temperature of about 150° C. Consequently, the transmission of the catalyst layer 14 and conjointly therewith the intensity I of the measuring beam 71 rises again to the previous value of 100% since the carbon monoxide which was adsorbed at the catalyst layer 14, is now oxidized.

During the remaining part of the venting phase 29 and when the temperature of the gas sensor 11 is lowered to the adsorption temperature of about 30° C., the transmission of the catalyst layer 14 and conjointly therewith the intensity I of the measuring beam 71 falls only by a very small amount to the value $B_2$ since, during this remaining part of the venting phase 29, the reference gas or a gas mixture is passed over the gas sensor 11 and which contains only traces of carbon monoxide or no carbon monoxide at all.

The electrical signals or output signals generated by the infrared radiation detector 90 correspond to the intensity of the measuring beam 71 and are supplied to the electronic evaluation circuit arrangement 3. During the suction phase 28 during which the gas sensor 11 assumes a temperature at which carbon monoxide is adsorbed by the catalyst layer 14, there is measured, preferably at the end of the time period at which the gas sensor 11 has the adsorption temperature, a value $B_1$ for this intensity. During the venting phase 29 during which the gas sensor 11 also assumes a temperature at which the catalyst layer 14 adsorbs carbon monoxide, there is measured a value $B_2$ of the intensity of the measuring beam 71, also preferably at the end of the time period during which the gas sensor 11 has the adsorption temperature.

From the two values $B_1$ and $B_2$ which correspond to the intensities indicated by $B_1$ and $B_2$ in FIG. 2a, the carbon monoxide concentration is now determined in the electronic evaluation circuit arrangement 3. The carbon monoxide concentration is given by the following equation:

$$[CO] \sim \alpha(B_2-B_1)/B_2 \qquad \text{Equation (1)}$$

wherein $\alpha$ is a proportionality constant.

Equation (1) will yield exact results only for values $(B_2-B_1)/B_2 \leq 0.1$. For greater values of the quotient $(B_2-B_1)/B_2$ the determination of the carbon monoxide concentration is according to Equation (2) wherein $\beta$ is a further proportionality constant:

$$[CO] = -\beta \log \frac{B_1}{B_2} = -\beta (\log B_1 - \log B_2) \qquad \text{Equation (2)}$$

Since the gas detector 100 primarily is intended for detecting small concentrations of carbon monoxide, this concentration is preferably determined in accordance with the Equation (1) by means of the electronic evaluation circuit arrangement 3.

The aforementioned equations are based on the at least approximate validity of Beer's Law. In cases in which this condition is not satisfied, any non-linearity can be accounted for by using a predetermined calibration or standardization curve.

The catalyst layer 14 reacts specifically with carbon monoxide, probably due to the formation of rhodium carbonyl compounds. The inventive method, therefore, provides an extremely specific detection of carbon monoxide with an extremely high sensitivity.

In order to prevent interferences the infrared radiation source 60 can be pulsed at a frequency which is considerably higher than the frequency of the gas exchange period 27. All of the output signals of the infrared radiation detector 90 are then processed by phase-selective rectification or demodulation and are thus converted into d.c.-signals, the magnitude of which is measured by means of a sample-and-hold device or circuit at the points indicated by $B_1$ and $B_2$ in FIG. 2a. The thus obtained measured values are then converted into digital signals by means of an A/D-converter and are then used for the determination of the carbon monoxide concentration in accordance with Equation (1) or (2) or any other appropriate relationship.

The electronic evaluation circuit arrangement 3 is designed such that an alarm is triggered when a predetermined concentration value is exceeded. Such concentration value is predetermined by the relationship $(B_2-B_1)/B_2$ or is approximately determined only by the difference $B_2-B_1$.

Instead of modulating the operation of the infrared radiation source 60 there can also be modulated the infrared radiation beam 69 and/or the measuring beam 71 by means of, for example, a mechanical chopper.

The gas displacement means or generator 4 may constitute a membrane constructed in the manner of a loudspeaker and provided with electromagnetically, electrostatically, piezoelectrically or thermomechanically operating exciting means. The gas displacement means or generator 4 may also comprise a piezo foil of the type made of polyvinylidenedifluoride. The gas displacement means or generator 4 may also contain a dimorphic, piezoelectric or bimetallic element. In miniaturized gas detectors the gas displacement means or generator 4 may also comprise a silicon membrane which is produced by means of a micro-lithographic process. In a practical example a commercial mini-loudspeaker has proven suitable as the gas displacement means or generator 4. A suitable oscillation frequency of the gas displacement means or generator 4 is a frequency in the range of about 0.01 to 10 Hz, preferably about 0.1 Hz.

The advantages of the inventive method and apparatus as compared to hitherto known spectroscopic methods and apparatus are as follows:

(i) by virtue of the comparison or reference measurements which are performed, for example, every thirty seconds at the point indicated by $B_2$ in FIG. 2a, by virtue of determining the concentrations from the difference between $B_1$ and $B_2$, and by virtue of the normalization due to the formation of the quotient $(B_2-B_1)/B_2$ there is completely compensated any zero drift which may be caused by the accumulation of dust, contamination and other negative effects on all of the optical components of the gas detector 100;

(ii) the gas detector 100, particularly the gas sensor 11 can be maintained at extremely small dimensions, for example, the gas sensor 11 need not exceed the dimensions of $2 \times 2 \times 2$ mm$^3$;

(iii) the measurements are extremely sensitive due to the use of the operating principle that the gas mixture to be investigated is periodically exchanged against a reference gas at the gas sensor 11 and that the difference of the output signals thus obtained is evaluated;

(iv) since the catalyst layer 14 of the gas sensor 11 must only have a size of some mm$^2$ and since the heating temperature does not have to exceed 150° C., the power consumption of the gas sensor 100 is extremely low;

(v) due to the restriction to a preselected infrared spectral region the gas sensor 11 is extremely selective, for example, for carbon monoxide if the preselected infrared spectral region is in the range of 1900 to 2200 cm$^{-1}$;

(vi) the gas detector 100 can also be used for the detection and/or determination of other gases when at least one further gas sensor is provided which is selective for the other gases. Such further gas sensors can be operated using the same infrared radiation source 60 and the same heating means 10 when a number of concave reflectors and infrared radiation detectors are employed. In this manner a specifically small spectroscope is obtained for fire protection, gas protection and environmental protection;

(vii) due to the adsorption of the gas at the catalyst layer 14 there is obtained a very high local gas or, for example, carbon monoxide concentration at the catalyst layer 14. Consequently, a thin catalyst layer 14 is found to be completely sufficient. By virtue of the suction there is continuously supplied a fresh sample of the gas mixture to be investigated and which may contain the reactive or reducing gas like, for example, carbon monoxide.

FIG. 3 shows a schematic cross-sectional view of a second embodiment of the gas detector 100 by means of which a further gas can be detected in addition to carbon monoxide. In this second embodiment of the gas detector 100 the measuring chamber 7 and the reference chamber 5 have the same cross-section, so that the connecting aperture is not present in this case. For better recognition of the details the measuring chamber 7 has been illustrated at a considerably larger scale in FIG. 3 which also is the case in the other figures of the drawings described hereinafter. The gas mixture to be investigated is supplied to the gas detector 100 through the inlet opening 9. The gas displacement means or generator 4 is located within the reference chamber 5.

Two infrared radiation beams 69 and 70 are emitted by the infrared radiation source 60. The infrared radiation beam 69 passes through a first infrared window 85 and impinges upon a first catalyst layer 14, passes through the first catalyst layer 14 and is reflected by the reflective layer 20 which is arranged below the first catalyst layer 14. The infrared radiation beam 69 is then passed through the first catalyst layer 14 a second time and, after a further passage through the first infrared window 85, impinges upon a first infrared radiation detector 90 which is provided with a first infrared filter 80. The second infrared radiation beam 70 is received by a second concave reflector 32 and reflected thereby in such a manner as to pass through a second infrared window 86 and to impinge upon a second catalyst layer 15. The infrared radiation beam 70 passes through the second catalyst layer 15 and is reflected at a second reflective layer 21 which is arranged below the second catalyst layer 15. The infrared radiation beam 70 is thereby reflected and passes through the second catalyst layer 15 a second time. Thereafter the infrared radiation beam leaves the measuring chamber 7 through the second infrared window 86 and impinges as a second measuring beam 72 upon a second infrared radiation detector 91 which is provided with a second infrared filter 81.

In the same manner as illustrated for the gas detector 100 in FIG. 1, the first and second infrared detectors 90 and 91 are connected to the electronic evaluation circuit arrangement 3 by means of electrical conductors or wires 12. The output signals supplied by the first and second infrared radiation detectors 90 and 91 correspond to transmission values of the first and second catalyst layers 14 and 15. These output signals are evaluated by the electronic evaluation circuit arrangement 3 for determining the concentration of carbon monoxide and of one further reactive gas which is present in the gas mixture to be investigated. If desired, the electronic evaluation circuit arrangement 3 can also be designed to emit an alarm signal under certain conditions.

The electronic evaluation circuit arrangement 3 contains, also in this case, switch elements by means of which the operation or movement of the gas displacement means or generator 4 and the heating means 10 and thereby the temperature of the gas sensor 11 are controlled. These switch elements and the connecting lines required therefor are of conventional design and, therefore, not specifically illustrated.

The first catalyst layer 14, the first infrared window 85 and the first infrared filter 80 in front of the first infrared radiation detector 90 are identical with the corresponding components of the gas detector 100 illustrated in FIG. 1. Therefore, this part of the second embodiment of the gas detector 100 is constructed for detecting and/or determining carbon monoxide.

The second catalyst layer 15, the second infrared window 86 and the second infrared filter 81 in front of the second infrared radiation detector 91 are designed for detecting and/or determining a further reactive or reducing gas in the gas mixture to be investigated. This is made possible by correspondingly selecting the material of the second catalyst layer 15 and the infrared spectral region of the second infrared radiation beam 70, for example, by corresponding selection of the material of the second infrared window 86 and of the second infrared filter 81 located in front of the second infrared radiation detector 91. Thus, for example, sulfur dioxide can be detected. Acetylene can be detected using a silica-supported palladium catalyst layer and an infrared filter 81 having its transmission in the range of 2950 to 3150 cm$^{-1}$. Ethylene can be detected and/or determined using a silica-supported platinum catalyst layer and an infrared filter 81 having its transmission in the range of 2750 to 3050 cm$^{-1}$.

Further gaseous components in the gas mixture to be investigated can be detected and/or determined by adding and correspondingly selecting further catalyst layers and by correspondingly modifying the gas detector 100 illustrated in FIG. 3.

A third embodiment of the inventive gas detector 100 is illustrated in FIG. 4 and such gas detector 100 comprises a concave reflector 31. The infrared radiation beam 69 emitted by the infrared radiation source 60 is received by the concave reflector 31 and reflected thereby in such a manner that the infrared radiation beam 69 passes through the infrared window 85 into the measuring chamber 7. The measuring chamber 7, the connecting aperture 8, and the reference chamber 5 have the same cross-section. The gas displacement means or generator 4 is located within the reference chamber 5. The measuring chamber 7 is connected to the external or environmental atmosphere through the inlet opening 9. The gas sensor 11 is provided with a catalyst layer 14, a reflective layer 20 arranged below the catalyst layer 14, and heating means 10.

The infrared radiation beam 69 passes through the infrared window 85 and through the catalyst layer 14 and is reflected by the reflective layer 20. After a further passage through the catalyst layer 14 a measuring beam 71 is formed which passes through the infrared window 85 and impinges upon the infrared radiation detector 90 which is provided with an infrared filter 80.

The mode of operation of the gas detector 100 illustrated in FIG. 4 is analogous to the mode of operation of the first embodiment of the inventive gas detector 100 which is illustrated in FIG. 1 and which was described in detail hereinbefore with reference to such FIG. 1.

Figure 5:
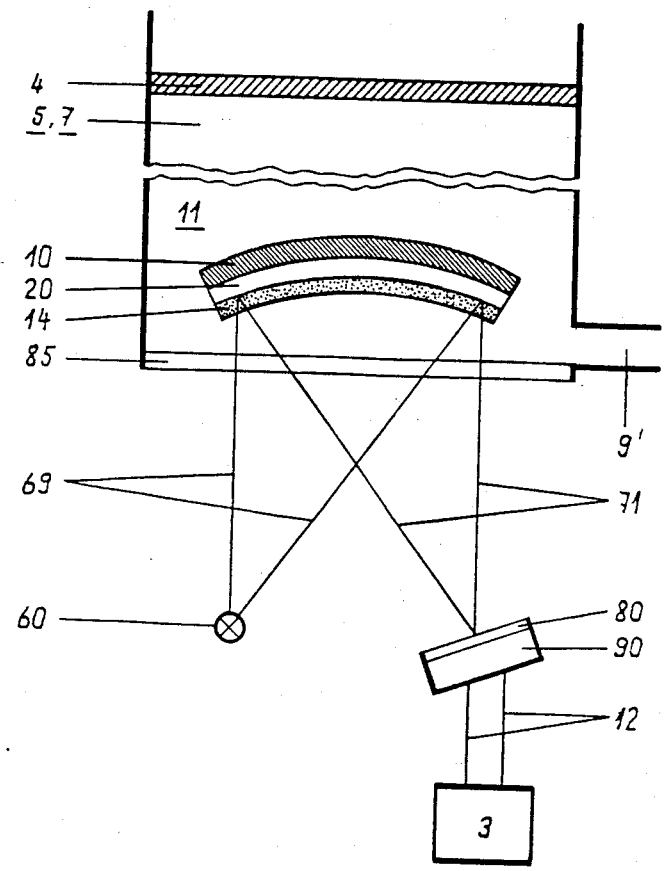
FIG. 5 is a schematic cross-sectional view of a fourth embodiment of the inventive gas detector and which contains a heatable concave reflector.

A fourth embodiment of the inventive gas detector 100 is illustrated in FIG. 5. In this embodiment the reflective layer 20 arranged below the catalyst layer 14 is constructed in the manner of a concave reflector and, consequently, no separate concave reflector is used in this specific embodiment. The infrared radiation beam 69 emitted by the infrared radiation source 60 passes through the infrared window 85 and impinges upon the catalyst layer 14. The reflective layer 20, as stated hereinbefore, constitutes a concave reflector and may assume the shape of part of a spherical surface, of an ellipsoid or a paraboloid. After reflection by the refractive layer 20 the measuring beam 71 passes through the infrared window 85 and through the infrared filter 80 and is focused upon the infrared radiation detector 90.

The reflective layer 20 and the catalyst layer 14 are heated to the required temperatures by the heating means 10. In this embodiment the inlet opening 9 constitutes a capillary tube 9' which has a length of about 1 cm and an internal diameter of about 0.5 mm. Due to the capillary tube 9' this fourth embodiment of the gas detector 100 is completely independent of the flow rate of the gas mixture to be investigated. The remaining components of the fourth embodiment of the gas detector 100 correspond to the components used in the gas detector embodiments described hereinbefore with reference to the foregoing figures of the drawings.

Figure 6:
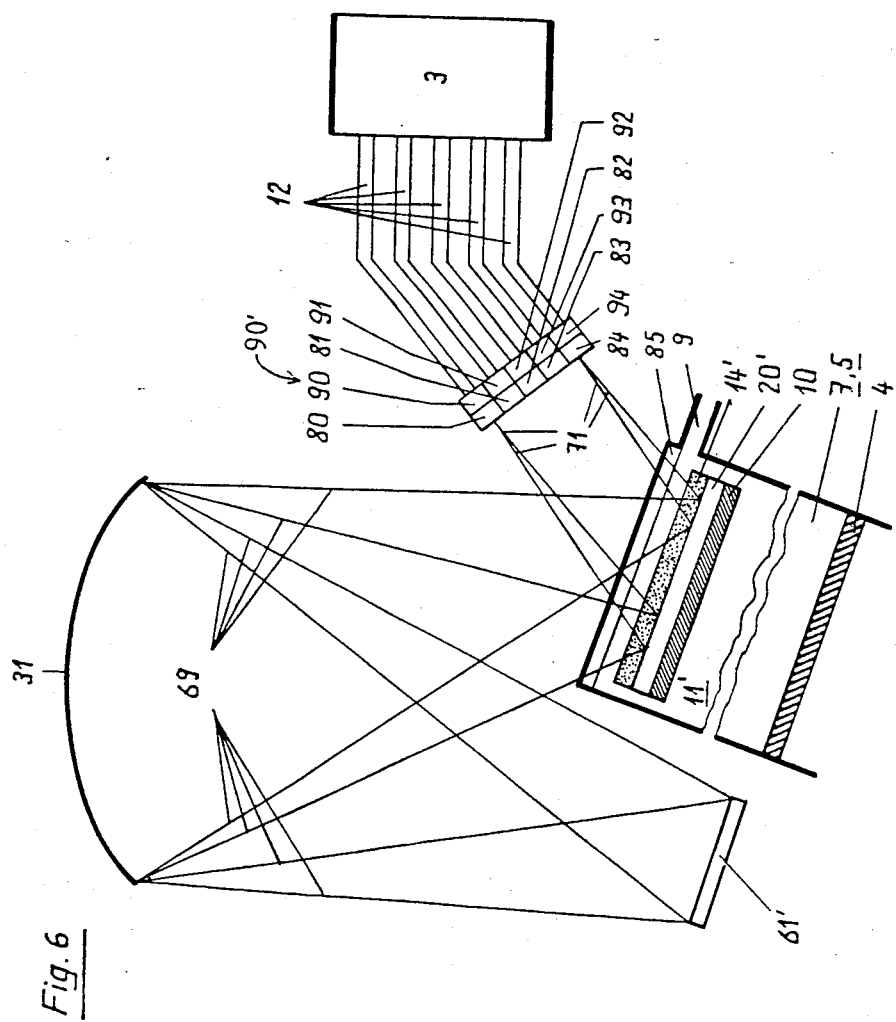
FIG. 6 is a schematic cross-sectional view of a fifth embodiment of the inventive gas detector which is similar to the gas detector arrangement shown in FIG. 4 and which contains a number of infrared detectors and infrared filters having different transmission ranges.

A fifth embodiment of the inventive gas detector 100 is illustrated in FIG. 6 and basically constitutes a modification of the third embodiment of the inventive gas detector described hereinbefore with reference to FIG. 4. In this fifth embodiment of the gas detector 100 the infrared radiation emitted by an elongate infrared radiation source 61' is received and reflected by the concave reflector 31 towards an oblong gas sensor 11' containing an oblong catalyst layer 14' and, therebelow, an oblong reflective layer 20'. The infrared radiation reflected by the oblong reflective layer 20' impinges upon broadband infrared detector means 90' which comprise an elongate arrangement of a predetermined number of, in the presently illustrated embodiment, five infrared radiation detectors 90 to 94 in a juxtaposed relationship. The elongate infrared radiation source 61' is designed, in combination with the concave reflector 31 and the oblong catalyst layer 14', such that the measuring beam 71 impinges upon the broad-band infrared detector means 90' comprising the elongate arrangement of juxtaposed infrared radiation detectors 90 to 94. Different narrow-band infrared filters 80 to 84 are arranged in front of related ones of the infrared radiation detectors 90 to 94. The oblong catalyst layer 14 is formed of a uniform material suited for the adsorption of different gases. The adsorption of the different gases causes different transmissions for the infrared radiation. The detection and/or determination of different gases to be detected in the gas mixture to be investigated is possible by virtue of the arrangement of different narrow-band infrared filters 80 to 84 which transmit infrared radiation in different infrared spectral regions, in front of related ones of the broad-band infrared radiation detectors 90 to 94.

Figure 7:
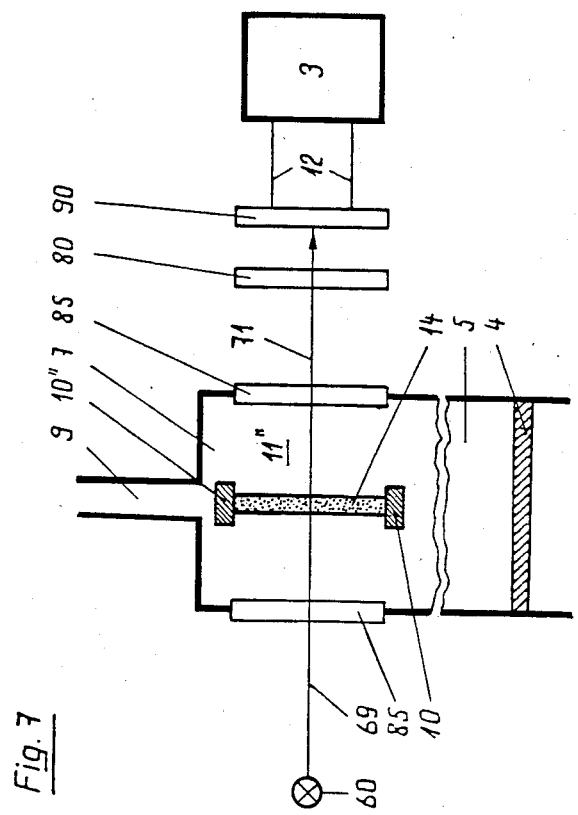
FIG. 7 is a schematic cross-sectional view of a sixth embodiment of the inventive gas detector in which the infrared radiation beam passes through the gas sensor.

FIG. 7 shows a schematic cross-sectional view of a sixth embodiment of the inventive gas detector 100. The infrared radiation beam 69 emitted by the infrared radiation source 60 passes through the gas sensor 11' in this embodiment. Again, the measuring chamber 7, the connecting aperture 8, and the reference chamber 5 have substantially the same cross-section. The measuring chamber 7 is connected to the external or environmental atmosphere via the inlet opening 9. Two substantially identical infrared windows 85 are located on opposite sides of the measuring chamber 7 and the gas sensor 11" is located therebetween. In this particular case the catalyst layer 14 contains finely divided platinum which is deposited upon alumina. The catalyst layer 14 is surrounded by heating means 10" which are arranged outside the path of rays of the infrared radiation beam 69. The infrared radiation source 60 is located on one side of the measuring chamber 7. The infrared radiation beam 69 emitted by the infrared radiation source 60 passes through the catalyst layer 14 and through both of the infrared windows 85 and impinges as the measuring beam 71 upon the infrared radiation detector 90 which is located on the rear of the infrared filter 80.

Figure 8:
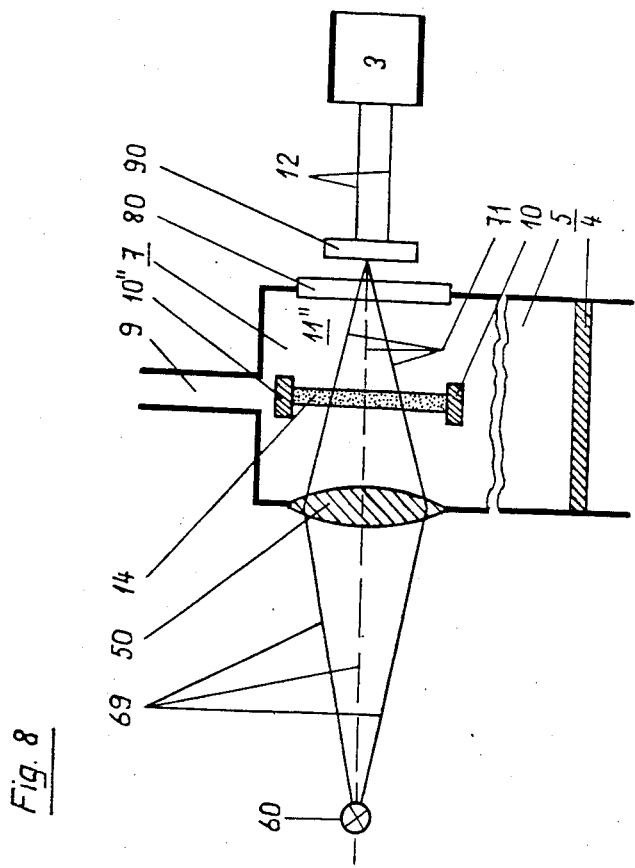
FIG. 8 is a schematic cross-sectional view of a seventh embodiment of the inventive gas detector in which an infrared radiation beam is formed by means of a collimator lens.

In order to improve the intensity or amount of available infrared radiation and to thus decrease the current consumption, an infrared lens 50 can be arranged intermediate the infrared radiation source 60 and the catalyst layer 14 located within the measuring chamber 7. In order to minimize reflection losses, the lens or lens means 50 is directly fitted into one wall of the measuring chamber 7 and the infrared filter 80 is directly fitted into the opposite wall of the measuring chamber 7. The infrared windows 85 used in the embodiments of the gas sensor 100 described hereinbefore can thus be omitted. This arrangement forms the seventh embodiment of the inventive gas detector 100 and is illustrated in a schematic and cross-sectional view in FIG. 8. The remaining components of such gas detector 100 correspond to the components used in the gas detector 100 which have been described hereinbefore.

Figure 9:
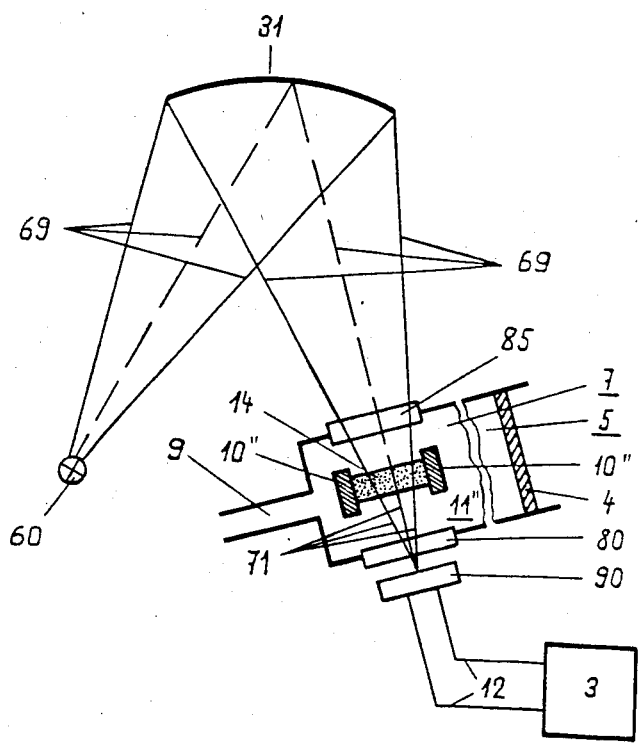
FIG. 9 is a schematic cross-sectional view of an eighth embodiment of the inventive gas detector which is similar to the gas detector shown in FIG. 7 and in which an infrared radiation beam is formed by means of a concave reflector.

FIG. 9 shows an eighth embodiment of the inventive gas detector 100 and this embodiment is a modification of the sixth embodiment of the gas detector 100 which is illustrated in FIG. 7. In this embodiment the infrared radiation beam 69 is received and reflected by the concave mirror 31 in such a manner that the measuring beam 71, after passing through the catalyst layer 14 of the gas sensor 11" and through the infrared filter 85 which is fitted into the wall of the measuring chamber 7, is focused upon the infrared radiation detector 90.

Figure 10:
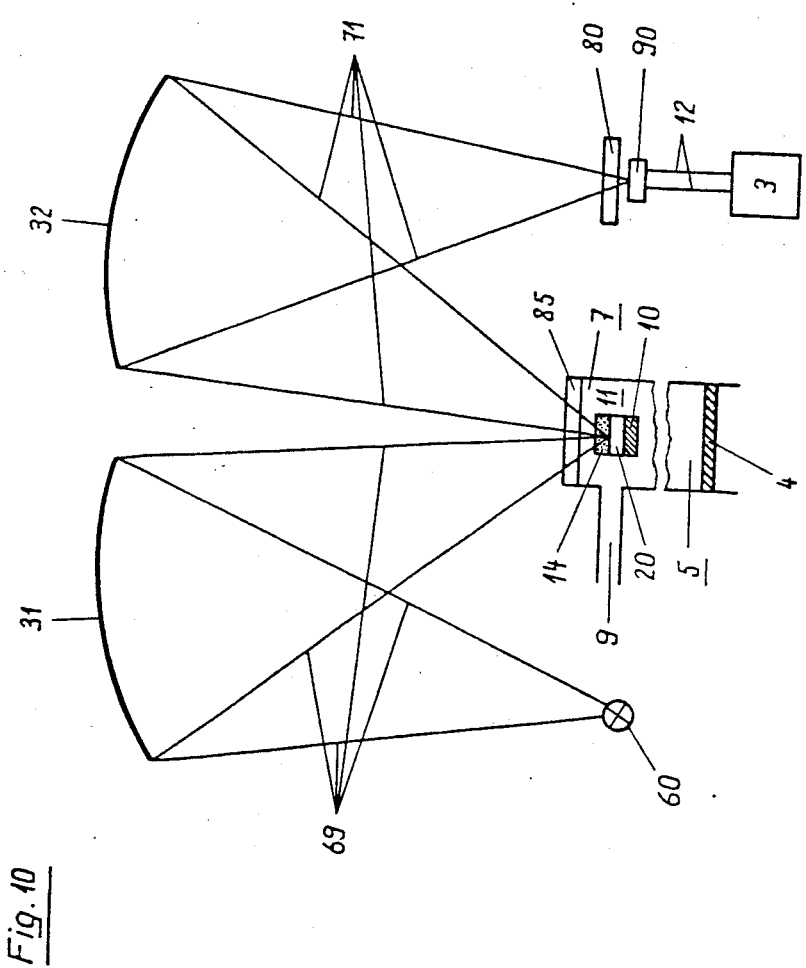
FIG. 10 is a schematic cross-sectional view of a ninth embodiment of the inventive gas detector which contains two concave reflectors.

A ninth embodiment of the inventive gas detector 100 is illustrated in FIG. 10. In this embodiment the infrared radiation beam 69 is focused upon the catalyst layer 14 of the gas sensor 11, on the one hand, and the measuring beam 71 originating from the reflective layer 20 and the catalyst layer 14 is focused upon the infrared radiation detector 90, on the other hand. The infrared radiation beam 69 which is emitted by the infrared radiation source 60, impinges upon the first concave reflector 31 which focuses the infrared radiation beam 69 in such a manner that this infrared radiation beam 69 passes through the infrared window 85 and impinges upon the gas sensor 11 located within the measuring chamber 7. The measuring chamber 7, the connecting aperture 8, and the reference chamber 5 have substantially the same cross-section as described in the aforedescribed exemplary embodiments. As a result, the gas detector 100 of the presently described embodiment comprises a common measuring and reference chamber. This combined measuring and reference chamber is connected to the external or environmental atmosphere through the inlet opening 9.

The diverging measuring beam 71 originating from the catalyst layer 14 of the gas sensor 11 impinges upon the second concave reflector 32 which is designed and arranged in such a manner that the measuring beam 71 passes through the infrared filter 80 and is focused directly upon the infrared radiation detector 90. The electrical output signal of the infrared radiation detector 90 corresponds to the intensity of this measuring beam 71 and is supplied via electrical lines 12 to the electronic evaluation circuit arrangement 3 and is evaluated therein in the usual manner as mentioned hereinbefore.

With the presently described type of arrangement there is involved a saving of energy because the catalyst layer 14 of the gas sensor 11 can be maintained at an extremely small size.

Also, in the embodiments of the inventive gas detector 100 described hereinbefore with reference to FIGS. 7 to 10 there can be arranged a plural number of infrared radiation detectors with associated different infrared filters for detecting and/or determining different components in the gas mixture to be investigated.

One possible structure of the electronic evaluation circuit arrangement 3 is illustrated in the form of a schematic block circuit diagram in FIG. 11 and such electronic evaluation circuit arrangement 3 can be used in combination with each of the inventive gas detectors 100 described hereinbefore with reference to FIGS. 1 to 10.

A synchronization unit 110 controls the temporal course of the temperature cycle by means of the voltage source 95 for the heating means 10 as well as the operation or movements of the gas displacement means or generator 4 by heans of a driver circuit 55. The output signal generated by the infrared radiation detector 90 and which corresponds to the intensity I of the measuring beam 71 is amplified by means of an amplifier 115 having an appropriate amplification or gain characteristic. This amplifier 115 converts the intensity I of the measuring beam 71 into a voltage 39 which is proportional thereto.

Two sample-and-hold units or circuits 120 and 121 are provided. The sample-and-hold units 120 and 121 receive the instruction for measurement from the synchronizer unit 110 and, under such instructions, generate voltages 40 and 41 which respectively correspond to the values $B_1$ and $B_2$ of the intensity I illustrated in FIG. 2a. A subtracting amplifier 130 generates a voltage 42 corresponding to the difference $B_2 - B_1$. In the dividing amplifier 135 the difference $B_2 - B_1$ is divided by the voltage 41 and there is thus delivered a voltage 43 which is proportional to the quotient $(B_2 - B_1)/B_2$.

A comparator 140 compares the aforementioned voltage 43 with a reference value 44 provided by a voltage source 145. If conditions for an alarm are present, the comparator 140 activates an alarm circuit 150.

In the case of an electronic evaluation circuit arrangement 3 intended to operate in accordance with Equation (2) the divider amplifier 135 is not needed and the amplifier 115 is used to generate a voltage 39 in such a manner that this voltage 39 is proportional to the logarithm of the intensity I of the measuring beam 71.

When the inventive gas detector 100 is equipped for detecting and/or determining a predetermined number of gases using the plural number of infrared radiation detectors 90 to 94 as illustrated in FIG. 6, the subcircuit designated by the reference numeral 300 in FIG. 11 and enclosed by broken lines is employed for each one of the predetermined number of gases.

The inventive gas detector 100 and the inventive method of detecting and/or determining reactive or reducing gases in a gas mixture to be investigated has been described in the foregoing exemplary embodiments with respect to the detection and/or determination of carbon monoxide. However, the method can be used in essentially the same manner for detecting and/or determining other reactive or reducing gases like, for example, ethane, ethylene, acetylene, other hydrocarbons or nitrogen monoxide. A preferred range of application of the inventive gas detector is in combination with apparatus for monitoring environmental contamination particularly in over-crowded settlement areas or regions. In such use of the inventive gas detectors there can be initiated predetermined smog alarm stages when a predetermined concentration is exceeded for a preselected number of pollutants or noxious gases.

While there are shown and described present preferred embodiments of the invention, it is to be distinctly understood that the invention is not limited thereto, but may be otherwise variously embodied and practiced within the scope of the following claims. ACCORDINGLY,

What I claim is:

1. A method of detecting at least one reducing gas in a gas mixture containing an oxidizing gas, by means of determining the attenuation of the intensity of an infrared radiation beam in a gas detector comprising an infrared radiation source, an infrared radiation detector, and an electronic evaluation circuit arrangement, said method comprising the steps of:

arranging in a measuring chamber a gas sensor which contains a catalyst layer comprising at least one transition metal selected from at least one of the groups I, VII and VIII of the Periodic Table of the Chemical Elements;

providing heating means for heating said gas sensor to a predetermined temperature;

admitting a gas mixture to be investigated through an inlet opening into said measuring chamber;

providing a reference chamber which is closed to the external atmosphere and which are provided with gas displacement means, said measuring chamber being connected to said reference chamber through at least one connecting aperature therebetween;

operating said gas displacement means and thereby increasing the volume of said reference chamber and drawing the gas mixture to be investigated into said measuring chamber through said inlet opening thereof and at least partially through said measuring chamber into said reference chamber during a suction phase of the operation of the gas displacement means;

maintaining said gas sensor by operating said heating means during a first part of said suction phase at a first operating temperature sufficiently high to oxidize the at least one reducing gas contained in the gas mixture drawn into said measuring chamber during said first part of said suction phase;

maintaining said gas sensor, during a remaining part of said suction phase, at a second operating temperature sufficiently low to preclude oxidation of said at least one reducing gas and thereby adsorbing into said catalyst layer of said gas sensor the at least one reducing gas present in the gas mixture drawn into said measuring chamber;

during said first part of said suction phase and during said remaining part of said suction phase, at least partially drawing from said measuring chamber through said at least one connecting aperture into said reference chamber a reference gas which contains a smaller or zero content of the at least one reducing gas due to the oxidizing action and the absorbing acton of said catalyst layer of said gas sensor;

further operating said gas displacement means and thereby decreasing the volume of said reference chamber and venting said reference gas from said reference chamber through said mesuring chamber and through said inlet opening thereof during a venting phase of the operation of said gas displacement means;

maintaining said gas sensor by means of said heating means, during a first part of said venting phase, at a third operating temperature at which the at least one reducing gas is oxidized;

maintaining said gas sensor, during a remaining part of said venting phase, at a fourth temperature at which the at least one reducing gas is adsorbed at said gas sensor;

generating a beam of infrared radiation by an infrared radiation source;

passing said beam of infrared radiation through said gas sensor and thereby forming a measuring beam of infrared radiation;

directing said measuring beam of infrared radiation to an infrared radiaton detector operatively connected to an electronic evaluation circuit arrangement and thereby determining the intensity of said measuring beam of infrared radiation;

determining a first value of said intensity of said measuring beam of infrared radiation during said remaining part of said suction phase of the operation of said gas displacement means and during which remaining part of said suction phase said gas sensor assumes said second temperature at which said at least one reducing gas is adsorbed thereat;

determining a second value of aid intensity of said measuring beam of infrared radiation during said remaining part of said venting phase of the operation of aaid gas displacement means and during which remaining part of said venting phase said gas sensor assumes said fourth temperature at which said at least one reducing gas is adsorbed thereat; and detecting said at least one reducing gas by correlating said first determined value and said second determined value of said intensity of said measuring beam of infrared radiation.

2. The method as defined in claim 1, wherein:
said step of maintaining said gas sensor at said third temperature during said first part of said venting phase includes the step of selecting a third temperature which is approximately equal to said first temperature of said gas sensor during said first part of said suction phase; and said step of maintaining said gas sensor at said fourth temperature during said remaining part of said venting phase includes the step of selecting a fourth temperature which is approximately equal to said second temperature of said gas sensor during said remaining part of said suction phase.

3. The method as defined in claim 1, further including the step of:
selecting said at least one transition metal from the group of transition metals having an atomic weight in the range of about 100 to about 205.

4. The method as defined in claim 1, further including the steps of:
selecting as said first and as said third temperature of said gas sensor a temperature of about 150° C.; and selecting as said second and as said fourth temperature of said gas sensor a temperature of about 30° C.

5. The method as defined in claim 1, wherein:
said step of detecting said at least one reducing gas by correlating said first and said second value of said intensity of said measuring beam of infrared radiation includes the step of determining a concentration of said at least one reducing gas in said gas mixture to be investigated by subtracting said determined first value from said determined second value of said intensity of said measuring beam of infrared radiation and dividing the thus obtained difference value by said determined second value of said intensity of said measuring beam of infrared radiation.

6. The method as defined in claim 5, further including the steps of:
setting a predetermined value of said concentration of said at least one reducing gas in said gas mixture to be investigated; and triggering an alarm whenever said predetermined value of said concentration of said at least one reducing gas in said gas mixture is exceeded.

7. The method as defined in claim 1, wherein:
said step of detecting said at least one reducing gas in said gas mixture to be investigated by correlating said first determined value and said second determined value of said intensity of said measuring beam of infrared radiation includes the step of determining a concentration of said at least one reducing gas in said gas mixture to be investigated by forming a negative logarithm of the quotient of said first determined value over said second determined value of said intensity of said measuring beam of infrared radiation.

8. The method as defined in claim 7, further including the steps of:
setting a predetermined value of said concentration of said at least one reducing gas in said gas mixture to be investigated; and triggering an alarm whenever said predetermined value of said concentration of said at least one reducing gas in said gas mixture is exceeded.

9. The method as defined in claim 1, wherein:

said step of operating said gas displacement means entails periodically operating said gas displacement means through a predetermined number of gas displacement cycles each of which consists of a predetermined duration and contains said suction phase and said venting phase; and said steps of maintaining said gas sensor at said first, second, third and fourth temperatures entails periodically heating said gas sensor through a predetermined number of heating cycles each of which consists of a predetermined duration and contains the successive steps of maintaining said gas sensor at said first temperature during said first part of said suction phase, maintaining said gas sensor at said second temperature during said remaining part of said suction phase, maintaining said gas sensor at said third temperature during said first part of said venting phase, and maintaining said gas sensor at said fourth temperature during said remaining part of said venting phase.

10. The method as defined in claim 9, further including the steps of:

selecting as said predetermined duration of each said gas displacement cycle a duration which is substantially twice said predetermined duration of each said heating cycle.

11. The method as defined in claim 9, further including the step of:

selecting as said predetermined duration of each said gas displacement cycle a duration which is shorter than twice the duration of each said heating cycle.

12. The method as defined in claim 1, wherein:

said step of determining said first value of said intensity of said measuring beam of infrared radiation entails measuring said intensity close to the end of said remaining part of said suction phase in the gas displacement cycle of the operation of said gas displacement means; and said step of determining said second value of said intensity of said measuring beam of infrared radiation entails measuring said intensity close to the end of said remaining part of said venting phase in the gas displacement cycle of the operation of said gas displacement means.

13. The method as defined in claim 12, wherein:

said step of detecting said at least one reducing gas by correlating said first and said second value of said intensity of said measuring beam of infrared radiation includes the step of determining a concentration of said at least one reducing gas in said gas mixture to be investigated by subtracting said determined first value from said determined second value of said intensity of said measuring beam of infrared radiation and dividing the thus obtained difference value by said determined second value of said intensity of said measuring beam of infrared radiation.

14. The method as defined in claim 13, further including the steps of:

setting a predetermined value of said concentration of said at least one reducing gas in said gas mixture to be investigated; and triggering an alarm whenever said predetermined value of said concentration of said at least one reducing gas in said gas mixture is exceeded.

15. The method as defined in claim 12, wherein:

said step of detecting said at least one reducing gas in said gas mixture to be investigated by correlating said first determined value and said second determined value of said intensity of said measuring beam of infrared radiation includes the step of determining a concentration of said at least one reducing gas in said gas mixture to be investigated by forming a negative logarithm of the quotient of said first determined value over said second determined value of said intensity of said measuring beam of infrared radiation.

16. The method as defined in claim 15, further including the steps of:

setting a predetermined value of said concentration of said at least one reducing gas in said gas mixture to be investigated; and triggering an alarm whenever said predetermined value of said concentration of said at least one reducing gas in said gas mixture is exceeded.

* * * * *

UNITED STATES PATENT AND TRADEMARK OFFICE
CERTIFICATE OF CORRECTION

PATENT NO. : 4,668,635

DATED : May 26, 1987

INVENTOR(S) : MARTIN FORSTER

Page 1 of 2

It is certified that error appears in the above-identified patent and that said Letters Patent is hereby corrected as shown below:

Title Page, Column 1, line 3 after "DETECTING" please delete "REATIVE" and insert --REACTIVE--

Title Page, Column 2, in the Abstract, line 3, please delete "are and insert --can be--

Title Page, Column 2, in the Abstract, line 16, please delete "precisionof" and insert --precision of--

Title Page, Column 2, in the Abstract, line 24, after "signal" please delete "this" and insert --thus--

Column 4, line 46, after "cm" please delete "$^1$" and insert --$^{-1}$--

Column 8, line 59, after "150°C" please delete "."

Column 9, line 6, after "30°C" please delete "."

Column 9, line 19, after "30°C" please delete "."

Column 11, line 8, after "150°C" please delete "."

Column 15, line 50, please delete "heans" and insert --means--

Column 16, line 59, after "which" please delete "are" and insert --is--

UNITED STATES PATENT AND TRADEMARK OFFICE
CERTIFICATE OF CORRECTION

PATENT NO. : 4,668,635

DATED : May 26, 1987

INVENTOR(S) : MARTIN FORSTER

It is certified that error appears in the above-identified patent and that said Letters Patent is hereby corrected as shown below:

Column 17, line 23, at the beginning of the line please delete "absorbing acton" and insert --adsorbing action--

Column 17, line 28, after "said" delete "mesuring" and insert --measuring--

Column 17, line 46, after "infrared" please delete "radiaton" and insert --radiation--

Column 17, line 57, after "of" (first occurrence) please delete "aid" and insert --said--

Column 17, line 60, after "of" please delete "aaid" and insert --said--

Column 18, line 22, after "150°C" please delete "."

Signed and Sealed this

Twenty-sixth Day of January, 1988

*Attest:*

DONALD J. QUIGG

*Attesting Officer*  *Commissioner of Patents and Trademarks*